(12) United States Patent
Ragsdale et al.

(10) Patent No.: US 8,017,381 B2
(45) Date of Patent: Sep. 13, 2011

(54) COMPOSITE ELECTROPORATION PLATE WITH INTERCHANGEABLE WELL INSERTS

(75) Inventors: Charles W. Ragsdale, Concord, CA (US); John Morrill, Alameda, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 1219 days.

(21) Appl. No.: 11/683,893

(22) Filed: Mar. 8, 2007

(65) Prior Publication Data

US 2008/0220493 A1    Sep. 11, 2008

(51) Int. Cl.
  *C12M 1/34*    (2006.01)
  *C12M 3/00*    (2006.01)
(52) U.S. Cl. .................................. 435/287.2; 435/285.2
(58) Field of Classification Search ........... 435/6, 285.5, 435/287.2, 288.4, 285.2, 173.6
  See application file for complete search history.

(56) References Cited

U.S. PATENT DOCUMENTS

| 3,527,067 A | * | 9/1970 | Atkinson | .......................... 70/71 |
| 4,682,891 A |   | 7/1987 | Macario et al. | |
| 6,118,582 A | * | 9/2000 | Del Buono | .................... 359/398 |

FOREIGN PATENT DOCUMENTS

WO    WO 2004/050866 A1    6/2004

* cited by examiner

*Primary Examiner* — Michael A Marcheschi
*Assistant Examiner* — Shanta G Doe
(74) *Attorney, Agent, or Firm* — Kilpatrick Townsend and Stockton LLP.; M. Henry Heines

(57) ABSTRACT

Electroporation on a plurality of samples of membranous structures is performed in an electroporation well plate that includes a frame that can hold a plurality of well strips to form a two-dimensional array of wells, and a set of well strips, the set containing strips that differ in the number of wells while having the same outer dimensions and hence being interchangeable, thereby allowing the user to select strips appropriate for a given electroporation procedure, and allowing the manufacturer to replace defective strips without rejecting an entire well plate when a small number of wells is found to be defective.

22 Claims, 4 Drawing Sheets

COMPOSITE ELECTROPORATION PLATE WITH INTERCHANGEABLE WELL INSERTS

BACKGROUND OF THE INVENTION

1. Field of the Invention

This invention lies in the field of electroporation, i.e., the process by which exogenous molecular species are inserted into membranous structures by suspending the structures in a liquid solution of the exogenous species and applying an electric field to the suspension. In particular, this invention addresses the apparatus for performing electroporation in a multitude of cell suspensions either simultaneously or in rapid succession.

2. Description of the Prior Art

Electroporation, or electric pulse-driven transfection, is widely used for impregnating membranous structures, such as living biological cells, liposomes, and vesicles, with exogenous molecules. The liquid in which the structures is suspended is typically an aqueous solution of the exogenous species in a high-conductivity buffer. Normal saline is commonly used as the buffer since, in addition to offering relatively low resistance to an electric current, normal saline provides an environment that is favorable to the viability of most membranous structures. The transfection of multiple samples of membranous structure suspensions either simultaneously or in rapid succession by electroporation is known as "high-throughput electroporation," a procedure that is useful in siRNA experiments, in research using cDNA libraries, and in numerous other manipulations of membranous structures that are practiced in biotechnology laboratories. In high-throughput electroporation, the samples undergo transfection in the wells of a multi-well plate that contains electrodes embedded in each well. Typical multi-well plates have the standard 96-well configuration of microplates, which serves the user well in many applications but offers only limited options when there is a need to transfect samples that are larger than the volumes of individual wells or samples that are smaller in number than the standard 96.

Plates for high-throughput electroporation also require a certain degree of precision in manufacturing, since uniform well size and electrode area and the absence of cross contamination between wells are important for controlled, reliable, and uniform transfection. The usually efficient and economical process of injection molding is conveniently used in electroporation plate manufacture but is complicated due to the need to form the plastic walls around the metal electrodes. Improperly formed plates are prone to wicking, for example, which occurs in a number of ways. One of these arises from the fact that the electrodes in the wells are often designed to leave a gap between the vertical edge of the electrode and the end wall of the well. The hot plastic used in the molding tends to draw away from the relatively cool electrode, and this drawing away can leave a narrow channel through or along an otherwise solid wall separating the wells. Capillary action through this channel can result in cross contamination between wells. Another wicking problem can arise when an electrode is not securely held against the wall of the well during the molding process. A small gap between the electrode and the wall can cause liquid from the cell suspension to be drawn up into the gap by capillary action, and possibly into an adjacent well. Improperly formed plates can also arise when hot plastic leaks into areas that are intended to be left open to form the wells. A single well that is defective for any of these reasons can require that an entire plate be discarded.

These and other limitations and sources of inefficiency in well plate design and manufacture are addressed by the present invention.

SUMMARY OF THE INVENTION

The present invention resides in a composite well plate for high-throughput electroporation in which the wells are manufactured in the form of a series of modular inserts that fit inside a frame, each insert being in the form of a strip containing one or more wells with electrodes inside the well(s). The frame is constructed to receive the inserts while leaving electrical contacts from the electrodes of the various inserts exposed for connection with external electrical contacts. The inserts are interchangeable and can range from a single well extending the length of the insert to a number of wells separated by partitions. Thus, the various inserts in the series can have the same outer dimensions but be subdivided to varying degrees into different numbers of wells. A typical series can include inserts with a single long well and no subdivisions, inserts with a single subdivision to form two wells, each half the length of the single insert, inserts with three subdivisions to form four wells, each one-fourth the length of the insert, and inserts with seven subdivisions to form eight wells, each one-eighth the length of the insert. Any subcombinations of these can be used, as well as other combinations, such as inserts that are subdivided along only a portion of their length. The interchangeability of the inserts allows the user to select the inserts that will contain the desired number of wells, as well as the desired well sizes, and insert the selected inserts into the frame, preferably completely filling the frame and thereby using the full lateral dimensions of the frame for electroporation, regardless of the number of samples to be treated. The user can thereby adapt the composite plate to any desired high-throughput electroporation procedure and any desired combination of samples.

In particularly preferred constructions, each insert is a longitudinal strip constructed with two electrodes on one longitudinal side and a single opposing electrode on the other longitudinal side directly across from the first two electrodes. The two electrodes on one side are referred to herein as a "split electrode" in view of their locations on the same side of the strip, each one extending half the length of the strip to collectively cover the entire length of the strip, except for a small gap between their otherwise abutting ends. The gap allows the two halves of the split electrode to be energized individually, presenting the user with the option of applying an electric pulse to ("shocking") half the wells within the strips at a time. The opposing electrode, extending the full length of the strip, will extend through all wells and serve as the opposing electrode in each well. Likewise, in strips subdivided into more than two wells, each half of the split electrode will extend through all of the wells occupying one half the length of the strip. In strips with a single well extending the length of the strip, the well can be shocked by energizing both halves of the split electrode simultaneously.

In these and other embodiments, the electrical contacts protruding from the inserts for connection to the external source of electric power will be identical among the various inserts to render the inserts interchangeable in terms of electrical connections as well. Preferably, the exposed or protruding contacts extend downward from the base of each insert, i.e., from the side opposite the side containing the well openings.

Among the advantages presented by high-throughput electroporation well plates of this invention, in addition to the ability of the user of mix and match inserts to obtain any desired combination of wells, is the ability of the manufacturer to reject and replace individual inserts that are defective in construction without rejecting an entire plate. A further advantage is that stresses to an individual insert during handling or use, or to a portion of an insert, will not be transmitted to other inserts, and single insert or a portion of a single insert that is damaged during handling, shipping, or use can be remedied by replacing the insert and not the entire plate.

These and other features, objects, embodiments, and advantages of the invention are explained in more detail below.

Figure 1:
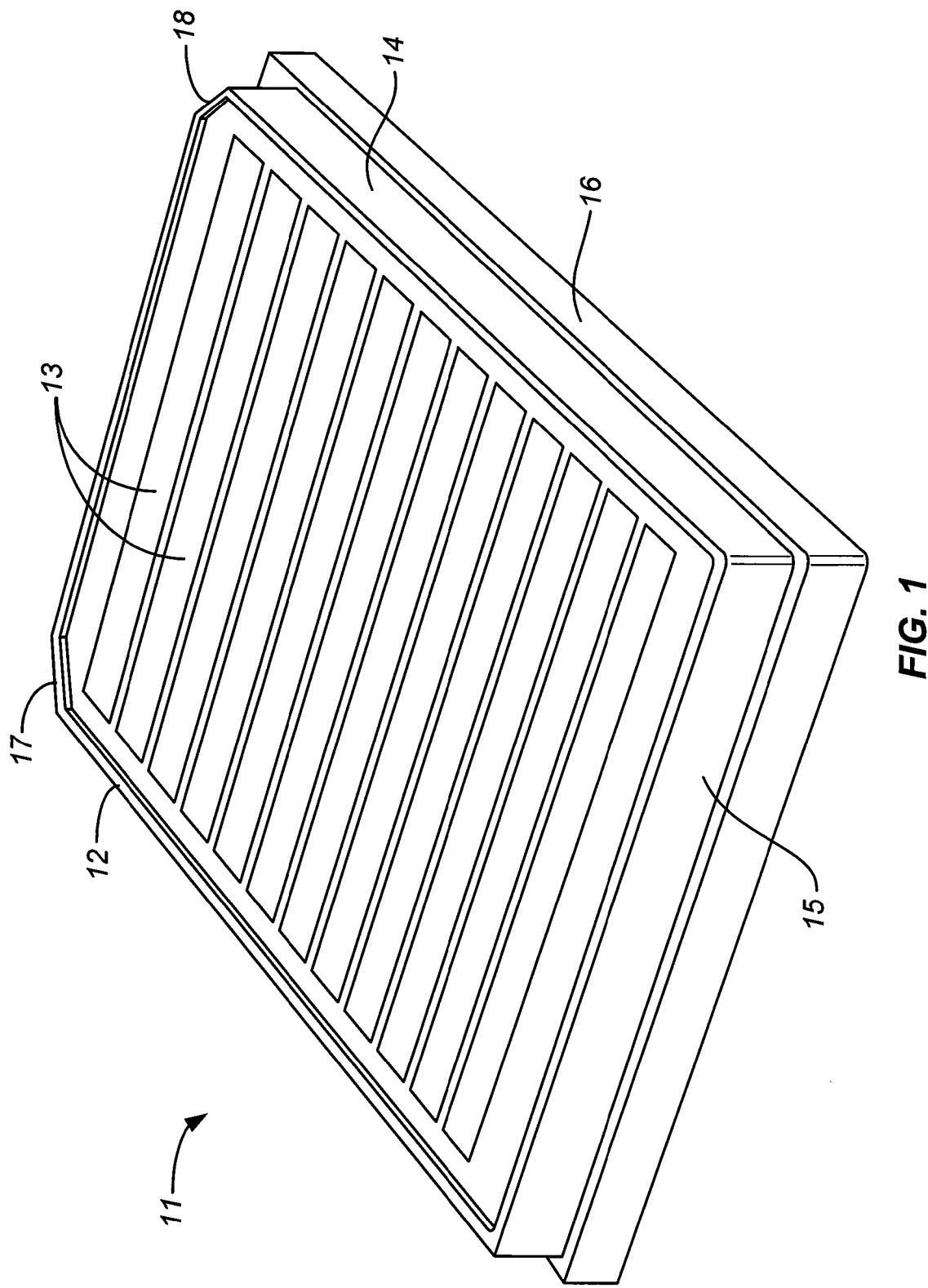
FIG. 1 is a perspective view of a composite high-throughput electroporation well plate of the present invention.

DETAILED DESCRIPTION OF THE INVENTION
AND PREFERRED EMBODIMENTS

The number of inserts in a set of inserts supplied with a single frame in accordance with this invention is not critical to the invention and can vary widely. The number of inserts that a single frame will accommodate is similarly not critical and can vary widely. It will generally be advantageous to supply a selection of inserts with differing numbers of wells per insert, with enough inserts to fill a single frame or multiple frames, thereby allowing the user a variety of choices. In most cases in the practice of this invention, a single frame will accommodate from four to fifty inserts, preferably six to twenty, and the number of inserts supplied with the frame can be as high as 100 or higher if desired, or as few as the number that the frame can accommodate at one time.

A single insert in accordance with this invention with more than two wells preferably has the wells arranged in a straight line that extends the length of the insert. Inserts that contain two or more rows of wells can also be included, but are not preferred.

The inserts and frame are most conveniently constructed in a manner that allows the inserts to be secured in the frame without the risk of slipping or sliding within the frame, or of falling out of the frame, and yet allows the inserts to be readily removed from the frame for replacement or cleaning. This type of construction can be accomplished by incorporating any of a wide variety of connections. Tabs or otherwise engaging parts that are resilient (i.e., spring-loaded) in construction are one example. Other examples are bosses and slots that may not be resilient. Still further examples are manually operated clamps, threaded connectors, or cam-operated fixtures.

The frame with attached inserts is preferably designed for insertion into an enclosed high-throughput electroporation chamber that protects the user against electric shocks. A chamber of this type can incorporate a printed circuit board with exposed leads that engage the electrical contacts extending from the inserts, and engagement and disengagement can be achieved by an interlock in the chamber lid that causes electrical engagement to occur upon closing of the lid and disengagement upon opening of the lid. The lid itself can be transparent to allow observation of the plate during electroporation. The chamber can also incorporate a programmer or controller to govern the sequence of electrodes to be energized and the voltage to be applied, as well as connections to an external power supply, or it may simply supply the connections to an external controller that serves these functions. A chamber with these features is described in commonly owned, co-pending U.S. Provisional Patent Application No. 60/826,353, filed Sep. 20, 2006, entitled "High-Throughput Electroporation Chamber."

While the features defining this invention are capable of implementation in a variety of constructions, the invention as a whole will be best understood by a detailed examination of specific embodiments. One such embodiment is shown in the drawings hereto.

FIG. 1 depicts a composite high-throughput electroporation plate 11 in accordance with the invention, in a perspective view as seen from the top of the plate. The plate consists of a frame 12 and twelve inserts in the form of well strips 13, all of the strips being of the same outer dimensions and configuration, and each one extending substantially the full width of the frame, and all situated parallel to each other. Although the individual wells are not shown in each strip, each strip either contains a single well extending substantially the full length and width of the strip, or is divided longitudinally into two or more wells along the length of the strip. The frame 12 is rectangular in shape with long side walls 14 and relatively short end walls 15 and a skirt 16, or slightly wider extension, extending downward from the lower ends of all four walls. The skirt 16 protects the electrical contacts (not visible in this drawing) that are extensions of the electrodes in each strip and protrude from the exterior of the each strip. The skirt 16 likewise covers the electrical contacts in the electroporation chamber (shown and described below) in which the plate 11 is inserted for use. Angled corners 17, 18 at one end of the frame guide the placement of the plate 11 in the chamber to assure that proper electrical contacts are made.

Figure 2A:
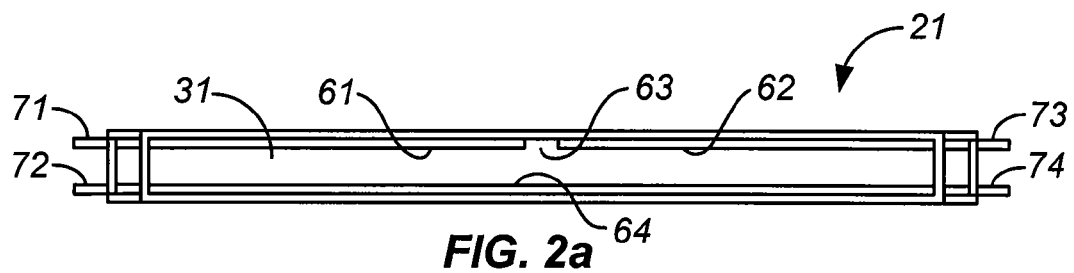
FIGS. 2a, 2b, 2c, and 2d are top views of four well strips for use as inserts in the composite plate of FIG. 1.
Figure 2B:
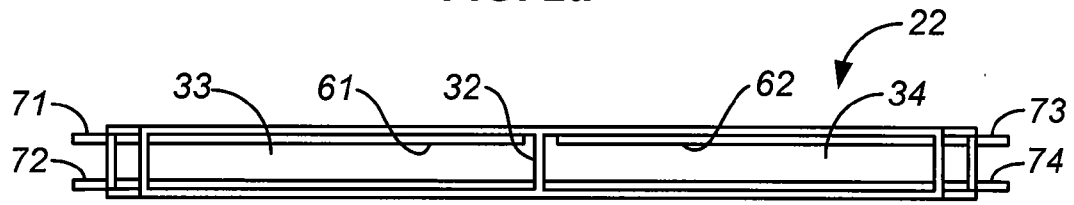
Figure 2C:
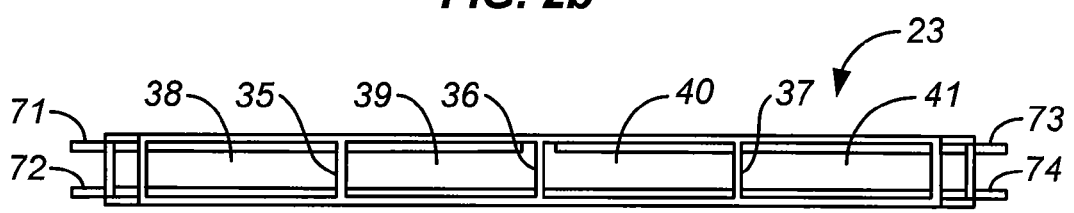
Figure 2D:
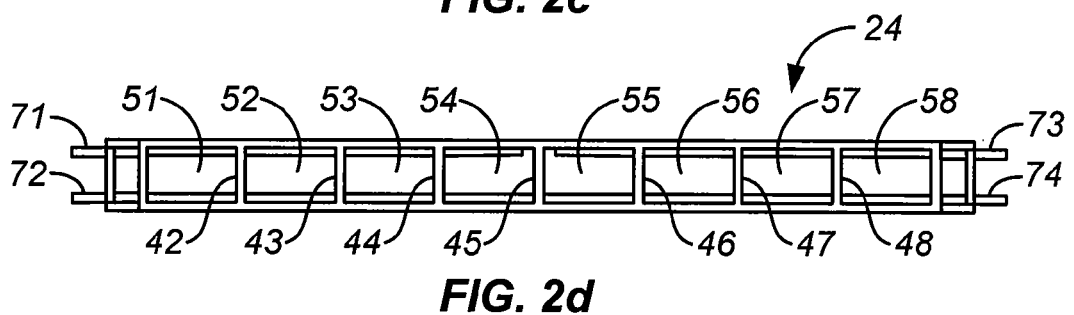
Figure 3:
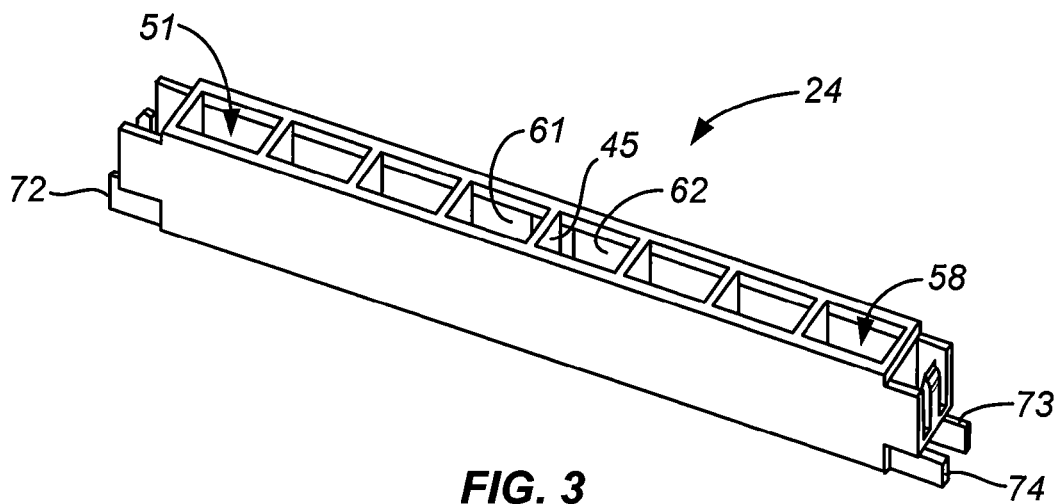
FIG. 3 is a perspective view of the well strip of FIG. 2d.

Individual well strips 21, 22, 23, and 24 are shown in FIGS. 2a, 2b, 2c, and 2d, respectively. These figures are top views of the strips, and the strip 24 of FIG. 2d is also shown in a perspective view from above in FIG. 3. The well strip 21 of FIG. 2a contains a single well 31, extending the full length of the strip; the well strip 22 of FIG. 2b has a partition 32 dividing the strip into two wells 33, 34 of equal size; the well strip of FIG. 2c has three partitions 35, 36, 37 dividing the strip into four wells 38, 39, 40, 41 of equal size; and the well strip of FIG. 2d has seven partitions 42, 43, 44, 45, 46, 47, 48, dividing the strip into eight wells 51, 52, 53, 54, 55, 56, 57, 58 of equal size. As noted above, these are merely examples; well strips can also be constructed and used in this invention that have both short wells and long wells in a single strip.

The electrodes in each of the well strips of FIGS. 2a, 2b, 2c, and 2d are substantially the same. As most clearly seen in FIG. 2a, a pair of electrodes 61, 62 forms a split electrode that occupies one longitudinal wall of the strip, extending substantially the full length of the strip with a gap 63 between the two inner ends of the electrodes. A full-length counter electrode 64 extends the full length of the opposing side of the strip. In FIG. 2a, the split electrode 61, 62 functions as a single electrode on one side of the well. In FIG. 2b, one of the electrodes 61 of the split electrode serves one well 33 while the other electrode 62 serves the other well. The counter electrode 64 penetrates the partition 32 and serves both wells 33, 34. The electrodes in FIGS. 2c and 2d (also shown in FIG. 3) are arranged analogously: each of the electrodes 61, 62 forming the split electrode in these Figures penetrates one or more partitions and extends into two wells in FIG. 2c and four wells in FIGS. 2d and 3. In each case, the counter electrode likewise passes through all partitions and extends into all wells. Also in each case, extensions 71, 72, 73, 74 of the electrodes extend beyond both ends of the strips and along the bottom ends of the strips to serve as electrical contacts with corresponding contacts in the chamber. The gap 63 between the two parts of the split electrode allow the two parts to be energized independently to shock half of the wells in a given strip at a time, if desired. With appropriate electrical circuitry and programming, therefore, as will be readily known to those of skill in the art, electroporation can be performed on samples that occupy only one-half of strip, thereby allowing the strip to be used for fewer samples than it can accommodate. The split electrode also allows the system to perform electroporation on the two halves of the strip in succession. The width of the gap is sufficient to prevent arcing and to allow the device as a whole to meet regulatory requirements relating to creepage and clearance. The gap is preferably at least 1.5 mm in width, and most preferably from about 1.5 mm to about 5.0 mm.

Figure 4:
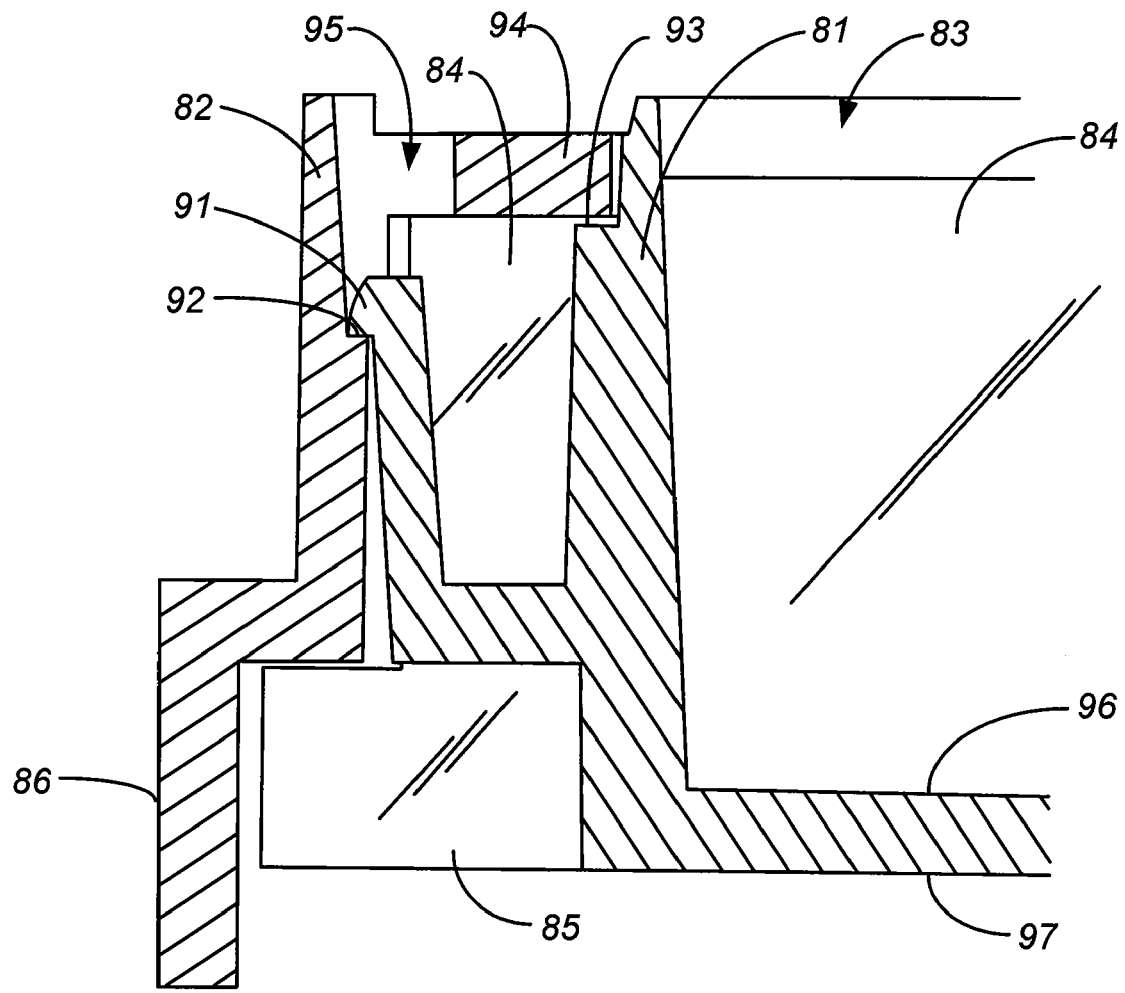
FIG. 4 is a cross section of one end of a well strip of the preceding figures and the frame in which the well strip is retained.

The means by which the well strips are secured to the frame in this embodiment are shown in FIG. 4. In this Figure, the strip 81 and the frame 82 are shown in cross section, with a portion of an end well 83 and one of the electrodes 84 visible. The extension 85 of the electrode is also visible, as is the skirt 86 along the lower edge of the frame 82 (corresponding to the skirt 16 in FIG. 1). Engagement of the strip 81 with the frame 82 is achieved by a hook 91 extending from the end of the strip and a shoulder 92 on the inner wall of the frame that engages the hook 91. The hook 91 is resilient in construction; thus, when the strip is inserted into the frame from the bottom, the hook 91 contacts the inner surface of the frame which causes the hook to bend slightly inward until the hook reaches the shoulder 92 where the hook is released. A second shoulder 93 on the well strip 81 near the end of the strip limits the upward movement of the strip by abutting the inner rim 94 of the frame. The well strip 81 is thus held in place by the hook 91 and the well strip shoulder 93. To allow release of the well strip 81 from the frame 82, the frame contains an opening 95 at the top surface of the frame directly above the frame shoulder 92 where the hook 93 is engaged. The user can insert an implement into this opening to pry the hook 91 back far enough to disengage the hook from the shoulder 92 and thereby allow the strip to be lowered out of the frame.

The wells within the well strip in this embodiment, and in preferred embodiments of the invention in general, are each equipped with a floor 96 that is polished to an optical finish. The term "optical finish" is used herein as it is used in the art, and in particular to denote that the floor is of a sufficiently high degree of flatness that the typical biological cell will grow and proliferate freely along the floor surface without its growth or proliferation being limited or inhibited by surface irregularities. The underside 97 of the floor is preferably at least a semi-optical finish, which term is used herein to denote that while the underside will not be used to cause cells to adhere, it will be sufficiently flat to allow the non-deflected passage of light from a vertical microscope when the plate material is transparent.

Figure 5:
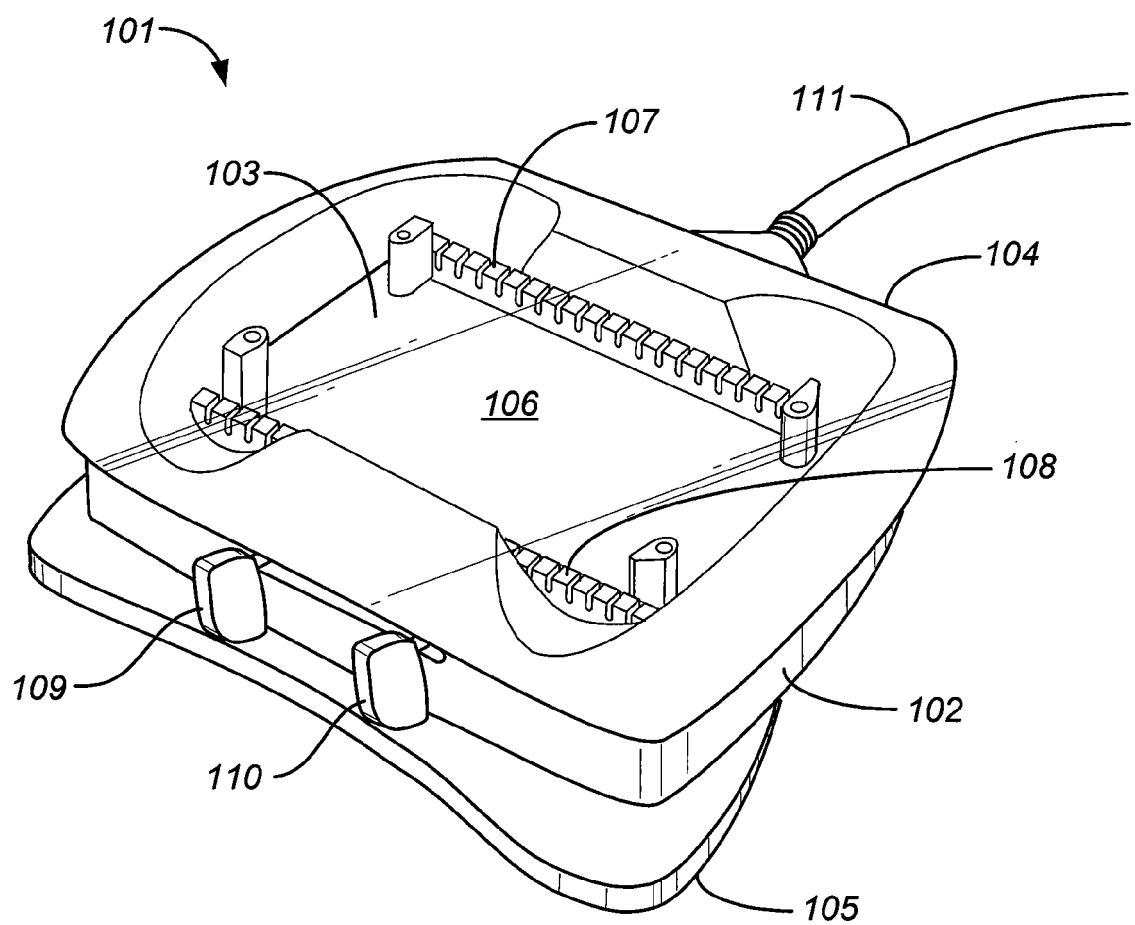
FIG. 5 is a perspective view of a chamber in which the composite plate of FIG. 1 is placed for performing a high-throughput electroporation procedure in the plate.

An example of a chamber with appropriate electrical connections for the composite electroporation plate of the preceding figures is shown and described in U.S. Provisional Patent Application No. 60/826,353, referenced above, and also shown in FIG. 5 hereto. This chamber 101 has a body 102 and a transparent lid 103 that are connected by a hinge connection (not shown) at the rear 104, with a supporting foot or base 105 below the body 102. The body 102 contains a well 106, visible through the transparent lid 103, to receive the composite electroporation plate, and along two opposing edges of the well are parallel rows 107, 108 of slots that are arranged to receive the electrical contacts 71, 72, 73, 74 (FIGS. 2a-2d and 3) protruding from the well strips of the composite electroporation plate. Below the well (and not visible in this Figure) is a printed circuit board with electrical contacts that are aligned with the slots to engage the electrical contacts 71, 72, 73, 74 on the bottoms of the well strips. Protruding through the wall of the body 102 of the chamber are a pair of finger tabs 109, 110 that are used for both releasing the lid 103 and urging the plate out of electrical contact with the slots 107, 108. A power cable 111 joined to the rear of the chamber body supplies power to the printed circuit board. The cable 111 leads to a high-throughput box (also not shown) that contains instrument electronics that control such features as the power level supplied to the chamber, the wave form of the power, the sequence of electric leads that will be energized (and hence the sequence of wells that will be shocked), and the timing of the sequence. The high-throughput box can also contain appropriate electronics to monitor the voltage to ensure that all wells receive electric power in accordance with the intended electroporation protocol.

The well strips and frame of the present invention can be formed of conventional materials of construction used for laboratory equipment. Polymeric materials that can be injection molded, such as polycarbonate, polysulfone, ULTEM® (General Electric Company, an amorphous thermoplastic polyetherimide) and similar materials, are particularly convenient. Conventional alternatives to injection molding can also be used.

The foregoing is offered primarily for purposes of illustration. Further variations and additional components can be incorporated into the structures without departing from the scope of the invention. The walls of the well strips, for example, can be molded to include features that will securely hold the electrodes in place during molding and subsequent thereto during handling. Shunts can be included in the frame either by snap connections, by the plastic sections of the frame around the shunts during injection molding, or by bonding the shunts to the frame. The electrodes can be formed with a surface roughness to improve the adherence of the plastic to the electrodes. Further examples will be readily apparent to those skilled in the art of electroporation procedures and electroporation chamber design.

In the claims below, the terms "a," "an," and "one" are intended to mean "one or more." The term "comprise" and variations thereof such as "comprises" and "comprising," when preceding the recitation of one or more steps or elements, are intended to mean that the addition of further steps or elements is optional and not excluded. All patents, patent applications, and other published reference materials in general that are cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition go a word or phrase and a definition explicitly provided in this specification of the same word or phrase, to the extent that any such definitions are included herein.

What is claimed is:

1. A composite high-throughput electroporation plate comprising:

a plurality of inserts of common external dimensions, each insert comprising one or more wells with embedded electrodes, wherein each said insert is an elongated body, and said plurality of inserts comprises at least one said insert with a single well extending substantially the length of said body, and at least one said insert with at least one partition dividing said insert into a plurality of wells positioned along the length of said body, a frame for receiving a fixed number of said inserts, and means for releasably securing each insert in said frame.

2. A composite high-throughput electroporation plate comprising:

a plurality of inserts of common external dimensions, each insert comprising one or more wells with embedded electrodes, wherein each said insert comprises an elongated body with an interior cavity defined by a pair of longitudinal walls and a pair of end walls, said embedded electrodes comprising a first electrode extending the length of one of said longitudinal walls and a pair of second electrodes longitudinally arranged along the other of said longitudinal walls, a frame for receiving a fixed number of said inserts, and means for releasably securing each insert in said frame.

3. The composite high-throughput electroporation plate of claim 2 wherein said second electrodes are separated from each other by a gap of at least 1.5 mm.

4. A composite high-throughput electroporation plate comprising:

a plurality of inserts of common external dimensions, each insert comprising one or more wells with embedded electrodes, wherein each said insert has an upper side to which said wells are open, and each said insert further comprises exposed extensions of said embedded electrodes extending to a lower side of said insert opposite said upper side, a frame for receiving a fixed number of said inserts, and means for releasably securing each insert in said frame.

5. A composite high-throughput electroporation plate comprising:

a plurality of inserts of common external dimensions, each insert comprising one or more wells with embedded electrodes, wherein each said well has a floor with an optical finish, a frame for receiving a fixed number of said inserts, and means for releasably securing each insert in said frame.

6. The composite high-throughput electroporation plate of claim 1 wherein said means for releasably securing each insert in said frame is a combination of a resilient hook and a shoulder to engage said resilient hook.

7. The composite high-throughput electroporation plate of claim 1 wherein each said insert is an elongated body, said frame has a width that is fully occupied by a single said insert, and said fixed number of inserts are received in a parallel arrangement by said frame.

8. The composite high-throughput electroporation plate of claim 1 wherein each said insert is of polymeric material injection molded around said electrodes.

9. A method for transfecting membranous structures with exogenous species in a plurality of samples in which said membranous structures and said exogenous species are suspended, said method comprising:

(a) placing said samples in individual wells of the composite high-throughput electroporation plate of claim 1; and (b) applying an electric potential across said embedded electrodes in each said well in which said samples are placed to cause transfection of said exogenous species into said membranous structures.

10. A method for transfecting membranous structures with exogenous species in a plurality of samples in which said membranous structures and said exogenous species are suspended, said method comprising:

(a) placing said samples in individual wells of a composite high-throughput electroporation plate comprising:

a plurality of inserts of common external dimensions, each insert comprising one or more wells with embedded electrodes, wherein each said insert comprises an elongated body with an interior cavity defined by a pair of longitudinal walls and a pair of end walls, said embedded electrodes comprising a first electrode extending the length of one of said longitudinal walls and a pair of second electrodes longitudinally arranged along the other of said longitudinal walls, a frame for receiving a fixed number of said inserts, and means for releasably securing each insert in said frame; and (b) energizing one of said pair of second electrodes in an insert in which one of said samples is placed without energizing the other electrode of said pair to cause transfection of said exogenous species into said membranous species.

11. A method for transfecting membranous structures with exogenous species in a plurality of samples in which said membranous structures and said exogenous species are suspended, said method comprising:

(a) placing said samples in individual wells of a composite high-throughput electroporation plate comprising:

a plurality of inserts of common external dimensions, each insert comprising one or more wells with embedded electrodes, wherein each said insert comprises an elongated body with an interior cavity defined by a pair of longitudinal walls and a pair of end walls, said embedded electrodes comprising a first electrode extending the length of one of said longitudinal walls and a pair of second electrodes longitudinally arranged along the other of said longitudinal walls, a frame for receiving a fixed number of said inserts, and means for releasably securing each insert in said frame; and (b) energizing each electrode of one of said pair of second electrodes in an insert in which one of said samples is placed, separately and in succession, to cause transfection of said exogenous species into said membranous species.

12. The composite high-throughput electroporation plate of claim 2 wherein said means for releasably securing each insert in said frame is a combination of a resilient hook and a shoulder to engage said resilient hook.

13. The composite high-throughput electroporation plate of claim 2 wherein each said insert is an elongated body, said frame has a width that is fully occupied by a single said insert, and said fixed number of inserts are received in a parallel arrangement by said frame.

14. The composite high-throughput electroporation plate of claim 2 wherein each said insert is of polymeric material injection molded around said electrodes.

15. The composite high-throughput electroporation plate of claim 4 wherein said means for releasably securing each insert in said frame is a combination of a resilient hook and a shoulder to engage said resilient hook.

16. The composite high-throughput electroporation plate of claim 4 wherein each said insert is an elongated body, said frame has a width that is fully occupied by a single said insert, and said fixed number of inserts are received in a parallel arrangement by said frame.

17. The composite high-throughput electroporation plate of claim 4 wherein each said insert is of polymeric material injection molded around said electrodes.

18. The composite high-throughput electroporation plate of claim 5 wherein said means for releasably securing each insert in said frame is a combination of a resilient hook and a shoulder to engage said resilient hook.

19. The composite high-throughput electroporation plate of claim 5 wherein each said insert is an elongated body, said frame has a width that is fully occupied by a single said insert, and said fixed number of inserts are received in a parallel arrangement by said frame.

20. The composite high-throughput electroporation plate of claim 5 wherein each said insert is of polymeric material injection molded around said electrodes.

21. A method for transfecting membranous structures with exogenous species in a plurality of samples in which said membranous structures and said exogenous species are suspended, said method comprising:
(a) placing said samples in individual wells of the composite high-throughput electroporation plate of claim 2; and
(b) applying an electric potential across said embedded electrodes in each said well in which said samples are placed to cause transfection of said exogenous species into said membranous structures.

22. A method for transfecting membranous structures with exogenous species in a plurality of samples in which said membranous structures and said exogenous species are suspended, said method comprising:
(a) placing said samples in individual wells of the composite high-throughput electroporation plate of claim 4; and
(b) applying an electric potential across said embedded electrodes in each said well in which said samples are placed to cause transfection of said exogenous species into said membranous structures.

* * * * *